United States Patent [19]

Smith et al.

[11] Patent Number: 4,690,821

[45] Date of Patent: Sep. 1, 1987

[54] TOWEL FOR SKIN MOISTURIZING AND DRYING

[75] Inventors: James A. Smith, Old Tappan; Betty J. Murphy, Upper Montclair, both of N.J.

[73] Assignee: Creative Products Resource Associates, Ltd., Fort Lee, N.J.

[21] Appl. No.: 846,508

[22] Filed: Mar. 28, 1986

Related U.S. Application Data

[63] Continuation of Ser. No. 579,033, Feb. 10, 1984, abandoned.

[51] Int. Cl.$^4$ ............................................. A61K 6/00
[52] U.S. Cl. .................................. 424/401; 514/941
[58] Field of Search ............... 424/28; 514/844-848; 252/90, 91; 514/937-943, 947

[56] References Cited

U.S. PATENT DOCUMENTS

| | | | |
|---|---|---|---|
| 3,691,270 | 9/1972 | Charlé et al. | 424/28 |
| 3,896,807 | 7/1975 | Buchwalter | 424/28 |
| 3,939,260 | 2/1976 | Lafton | 424/28 |
| 4,268,526 | 5/1981 | Vargas et al. | 514/943 |
| 4,272,544 | 6/1981 | Cella | 424/83 |
| 4,278,570 | 7/1981 | Flom | 514/943 |
| 4,323,693 | 4/1982 | Scala, Jr. | 424/59 |
| 4,331,653 | 5/1982 | Brown et al. | 424/28 |
| 4,368,187 | 1/1983 | Flom et al. | 424/60 |
| 4,405,324 | 9/1983 | Cruz, Jr. | 424/28 |
| 4,462,981 | 7/1984 | Smith | 424/28 |

FOREIGN PATENT DOCUMENTS 1577926 10/1980 United Kingdom ................. 424/28

Primary Examiner—Leonard Schenkman
Attorney, Agent, or Firm—Merchant, Gould, Smith, Edell, Welter & Schmidt

[57] ABSTRACT

Cosmetic applicators effective to simultaneously moisturize and absorb water from wet skin are provided which comprise a porous substrate impregnated with a water-free composition comprising a hydrophillic emolient oil and a hydrophobic emollient oil.

11 Claims, No Drawings

TOWEL FOR SKIN MOISTURIZING AND DRYING

This is a continuation of application Ser. No. 579,033, filed Feb. 10, 1984, now abandoned.

The problem of lubricating and softening skin areas which are repeatedly exposed to soap, synthetic detergents, solvents, antiseptics and the like has been addressed by a number of moisturizing creams and lotion-containing products. Typically, either the skin is first dried and then moisturizer applied, or the skin is wiped with a pre-wetted towel, which applies an alcohol-water solution or emulsion of an emollient. Either the skin remains wet and must be further dried, thus removing some or all of the emollient, or the skin is dried via evaporation of the alcoholic solvent, a relatively slow process which may lead to skin irritation.

Therefore, it is an object of the present invention to provide a cosmetic applicator which will effectively dry wetted skin while simultaneously and evenly applying a moisturizing and lubricating amount of emollient oils.

It is a further object of the present invention to provide a water-absorbent towel treated with emollient oils and antimicrobial agents which will simultaneously dry, soften and disinfect wet skin surfaces, e.g. of the user's hands.

Other objects, advantages and novel features of the present invention will be apparent to those skilled in the art from the following description and appended claims.

BRIEF DESCRIPTION OF THE INVENTION

The objects of the present invention are attained by providing a cosmetic applicator comprising a sheet of absorbent material. The fibers or cell walls of the absorbent material are coated with a water-free composition comprising at least one water-soluble or self-emulsifying emollient oil, while maintaining the interstices between the fibers or cells of the base sheet substantially free of the composition. The emollient composition may further comprise minor but effective amounts of fragrance, detergents and/or antimicrobial agents. The fiber type, weight and porosity of the base sheet is selected so that the sheet will hold and release an effective amount of emollient oil while retaining its ability to absorb substantially all of the water present on the skin when the applicator is pressed against wet skin under conditions of pressure, thus drying the skin. The emollient oil compositions of the present invention are formulated so that an effective amount may be applied to the sheet fibers and evenly transferred therefrom onto the skin without imparting an unduly sticky or greasy feeling to either the treated sheets or to the mosturized skin. As used herein with respect to the emollient compositions or finished applicators, the term "water-free" indicates that no amount of water is present which would adversely effect the above-described properties of the instant applicators, e.g. that no more than about 0.5-5% water will be included. Preferably the present compositions and applicators are prepared without the use of added water, other than that present as impurities in the components employed or which may be bound thereto by hygroscopic attraction. The term "impregnate[d]" when used with respect to the porous substrates of the present invention indicates that the fibers or cellular matrix of the substrate are coated with the present compositions to an exent which does not substantially inhibit the applicators' ability to absorb water.

DETAILED DESCRIPTION OF THE INVENTION

The emollient compositions of the present invention which are applied to the porous substrate may be composed entirely of emollient oils, although preferably they will incorporate a minor amount of a chemically-compatible fragrance for cosmetic appeal. Emollient oils generally function to soften and lubricate the skin surface and to prevent evaporative loss of skin moisture supplied by underlying tissue. They also function to provide a protective barrier against environmental irritants.

Preferably emollient oils will comprise about 90-99% by weight of the present compositions, most preferably about 95-98%, and will comprise a mixture of at least one hydrophillic (water soluble or self-emulsifying) emollient oil and at least one hydrophobic (water insoluble) emollient oil. Each type of oil will preferably be included to the extent of about 35-60% of the total composition, most preferably they will be present in about equal amounts.

Preferred self-emulsifying or water-soluble emollient oils will include about 30-50% of the fatty acid-, fatty alcohol- and/or (lower)polyoxyalkylene esters or alkoxylates of $C_2$-$C_{10}$ polyols comprising from about 2-5 free hydroxyl groups. These compounds are selected from those that readily dissolve or emulsify in skin moisture and, when they comprise polyoxyalkylene chains, aid in emulsifying the water-insoluble oils or waxes which may be present, so as to effectuate their delivery from the matrix of the base sheet to the skin of the user. One especially preferred water-soluble class of emollient oils are the mixed polyoxyethylene, fatty acid esters of glycerol wherein the fatty acid portion preferably comprises an about 15-22 carbon chain and about 5-10 ethylenoxy moieties are present in the polyoxyethylene chain. Preferably, these glycerates will comprise about 25-35% by weight of the present compositions. Such mixed esters are exemplified by PEG-7 glyceryl cocoate, available as Standamul HE (Henkel Corp., Hoboken, N.J.)

Another useful class of hydrophillic emollient oil is the $C_6$-$C_{12}$-acid diesters of propylene glycol, such as propylene glycol dicaprylate, propylene glycol dicaprate, mixtures thereof or the mixed caprate, caprylate ester. Propylene glycol dicaprylate-dicaprate is available as Standamul 302 (Henkel Corp.). These mixed esters will preferably comprise about 5-10% of the present emollient compositions.

A further useful class of self-emulsifying emollient oils are the mixed fatty acid-fatty alcohol esteralkoxylates of polyoxyethylene glycol wherein the acid and alcohol components each comprise 12-18 carbon atoms and the polyoxyethylene glycol component is made up of 2-5 ethylenoxy units. This class of emollient will preferably comprise about 1-5% of the present compositions and may be exemplified by polyoxyethylene (3) myristyl ether myristate (Standamul 1414 E, Henkel Corp.)

Other water-soluble, self-emulsifying emollient oils which are useful in the present compositions include the polyoxyalkoxylated lanolins and the polyoxyalkoxylated fatty alcohols. The polyoxyalkoxy chains preferably will comprise mixed propylenoxy and ethylenoxy units. The lanolin derivatives will typically comprise about 20-70 such lower-alkoxy units while the $C_{12}$-$C_{20}$-fatty alcohols will be derivatized with about 8-15 lower-alkyl units. One such useful lanolin derivative is Lanexol AWS (PPG-12-PEG-50) of the general formula Lanolin$[OCH(CH_3)CH_2]_x(OCH_2CH_2)_yOH$ wherein x is about 12 and y is about 50 (Croda, Inc., New York, N.Y.). A useful poly(15–20)$C_2$–$C_3$-alkoxylate is PPG-5-Ceteth-20; $CH_3(CH_2)_{14}CH_2[OCH(CH_3)CH_2]_x(OCH_2CH_2)_yOH$ wherein x is about 8 and y is about 2 (Procetyl AWS, Croda, Inc.). Preferably about 4–10% of one or, more preferably, both of these polyoxyalkoxylated emollients will be employed in the present compounds, i.e. about 5–7% of a 1:1 mixture of the lanolin derivative and the fatty alcohol derivative.

Therefore, the present emollient compositions will preferably comprise about 35–60% by weight, most preferably about 40–55% by weight of one or more of the above-described classes of water soluble or self-emulsifying emollient oil.

The water-soluble emollient component of the present compositions may also include a minor amount, for example about 0.5–5% of a polyoxyethoxylated soya sterol formed by derivatizing the $C_3$-OH group of sitosterol or campersterol with 5–25 ethanoloxy groups. Preferably about 0.75–2% of a polyoxyethylene-10-16-soya sterol (Generol 122E-10 or Generol E-16, General Mills) will be included in the present compositions. The balance of the emollient oil component of the above-identified commositions will comprise about 40–60% of one or more water-insoluble ("hydrophobic") emollient oils. A preferred class of water-insoluble emollient oil is the benzyl alcohol ester of one or more $C_{10}$–$C_{20}$ fatty acids, which will comprise about 15–25% by weight of the total emollient composition. An especially preferred member of this class of emollients is benzyl linoleate (Dermol 618, Alzo, Inc., Matawan, N.J.). These esters are preferably used in combination with about 10–25%, most preferably with an about equal amount of their reverse esters, i.e. the fatty alcohol esters of benzoic acid such as the $C_{12}$–$C_{15}$ alkylbenzoates (Finsolv TN, Finetex, Inc.) described in U.S. Pat. Nos. 4,278,655 and 4,275,222. Together, these two classes of aromatic emollient oils will preferably comprise about 25–35% by weight of the compositions of the present invention.

Although the fatty alcohol-benzoates are preferred components of the present invention, they may, in some cases, be partly or entirely replaced by the liquid fatty alcohol esters of $C_3$–$C_6$ aliphatic carboxylic acids, i.e. by isodecyl neopentanoate (Dermol 105). These compounds may be used in amounts up to about 40% of the total composition.

Likewise, the fatty acid benzoates may be partly or entirely replaced by the waxy $C_2$–$C_5$ alkyl esters of fatty acids, such as isopropyl myristate (Crodocol IPM, Croda, Inc.). The use of the upper range limits of these compounds is not preferred, since they tend to impart a somewhat sticky feeling to the finished applicators.

Another preferred class of water-insoluble liquid emollient oils for use in the present invention is the alkanol di- or tri- esters of dimer or trimer acid (the dimer or trimer of oleic acid).

Useful compounds of this class will include about 7–20% preferably about 10–15% of the di- or triesters of dimer acid or trimer acid formed by esterfying the acid with a $C_2$–$C_5$ alkanol, preferably isopropanol. Such compounds are commercially available as Schercemol TT (Triisopropyl Trimerate) and Schercemol DID (Diisopropyl Dimerate, Scher Chemicals, Clifton, N.J.). The liquid fatty acid-esters of dimer acid may also be successfully employed in the present compositions, e.g. the diisostearyl ester of dimer acid, Schercemol DISD. These esters of dimer acid may be partly or wholly replaced by the liquid esters of polyethylene glycol, e.g. by polyethylene glycols of average molecular weight of 300–600.

The water-insoluble emollient oils may also comprise a minor amount of silicone oil or mineral oil, preferably about 1–10%, which acts as a barrier against skin irritants as well as controlling the foaming caused by any added detergents, or ionic antimicrobial agents.

Preferably both the water-soluble or self-emulsifying (hydrophillic) emollient oils and the water-insoluble emollient oils will be selected from the general class of emollients termed nonionic emollients. The selection of this class of emollient permits the present compositions to be formulated by simple mixing techniques while avoiding the problem of chemical incompatibility of the emollients. However, in order to achieve complete homogeniety of the emollient compositions, it has been found highly desirable to include a minor but effective amount of one or more amphoteric detergents in the present compositions, for example in an amount equal to about 0.1–5%, preferably about 0.25–2% of the total composition weight. Preferred amphoteric detergents are the amine oxides, such as the $C_{10}$–$C_{20}$-alkyl-di(lower)alkyl-amine oxides or the [$C_{10}$–$C_{20}$-alkylamido(C-$_2$–$C_5$)alkyl]di(lower)alkyl-amine oxides. Especially preferred members of this class include lauryl(dimethyl)amine oxide, myristyl(dimethyl)amine oxide, stearyl(dimethyl)amine oxide (Schercamox DMS, Scher Chemicals, Inc., Clifton, N.J.), coco(bis-hydroxyethyl)amine oxide (Schercamox CMS), tallow(bis-hydroxyethyl)amine oxide and cocamidopropyl(dimethyl)amine oxide(Schercamox C-AA). As well as acting as homogenizing agents, these detergents act to foam the emollient compositions upon contact with moisture and aid in cleansing the skin.

Minor but effective amounts of compatible antimicrobial agents may also be included in the present emollient compositions in order to reduce to bioburden of the applicators during storage. Preferred antimicrobial agents are selected from those which will solubilize during use and transfer to the skin during use. Moistuizing applicators formed with such agents are especially preferred for use by medical personnel in situations where it is desirable to simultaneously moisturize and dry the hands, while maintaining the skin in a substantially sterile condition, i.e. as in after scrubbing for surgery.

When the the present compositions are formulated employing nonionic emollients and, optionally, amphoteric detergents, a wide variety of antimicrobial agents may be included in effective amounts without inducing undesirable interactions or chemical reactions between the major components of the compositions. Such agents include chlorhexidine gluconate, glutaral, halazone, hexachlorophene, nitrofurazone, nitromersol, povidone-iodine, thimerosol, $C_1$–$C_5$-parabens, clofucarban, chlorophene, poloxamer-iodine, phenolics, mefanide acetate, aminacrine hydrochloride, oxychlorosene, metabromsalene, merbromine, dibromsalan and the like. Preferred cationic germicidal agents include the salts of substituted amines.

The germicides are preferably selected from the general class of ammonium salts which possess both surface-active and emollient properties. Such components can be represented by the general formula (I) where R represent a lipophilic group such as a long-chain alkyl, alkylamido, alkylamidoalkyl or polycyclic radical, as well as their derivatives; $R_1$, $R_2$, $R_3$ represent H, benzyl, alkyl, hydroxyalkyl or heterocyclic groups, $A^-$ is an counter ion such as acetate, $Cl^-$, $SO^=_4$, $Br^-$, $PO_4{}^{+3}$ and n is 1-3. N may also be part of a heterocyclic ring, i.e. a pyridine ring or the azoniatricyclo[3.3.1.1]-decane system.

$$[RNR_3]_n{}^+ A^-  \quad (I)$$
with $R_2$ above and $R_1$ below.

Especially preferred compounds are the $C_8$-$C_{20}$-alkyl (dimethyl)-(benzyl or substituted-benzyl)ammonium halides such as benzalkonium chloride, cetalkonium chloride and the like. Other useful nitrogenous germicides include benzethonium chloride, cetylpyridinium chloride, methylbenzethonium chloride, cetylpyridinium chloride, methylbenzethonium chloride, cetyl(-dimethyl)ethyl ammonium bromide, domiphen bromide, gentian violet, dicoco(dimethyl)ammonium chloride, cetyl(trimethyl)ammonium buomine and the like.

Other useful amine salts are the stearyl amine salts that are soluble in water such as stearyl amine acetate, stearyl amine hydrochloride, stearyl-dimethylamine hydrochloride, distearyl amine hydrochloride, decyl pridinium bromide, the pyridinium chloride derivative of the acetylaminoethyl esters of lauric acid, lauryl trimethyl ammonium chloride, decylamine acetate and bis(oleoyl)-(5-8)-ethanoloxy-substituted-tallow ($C_{14}$-$C_{18}$)amine-hydrogen phosphate (Necon CPS-100) and the like.

Although the amount of germicide incorporated in the present emollient compositions will vary greatly, being dependent on factors such as its water-solubility, toxicity and the like, it will generally be sufficient to incorporate about 0.01-5%, preferably about 0.025-3% of the germicide. Compounds of formula I are generally effective as germicides when a concentration of about 300-1000ppm is attained in the emollient emulsion which is deposited on the skin of the user.

Minor but effective amounts of fragrance selected so as to be chemically-compatible with the above-described emollients are preferably included in the compositions of the present invention for cosmetic purposes. Useful fragrances will include, for instance about 0.025-2%, preferably about 0.05-1.5% of floral oils such as rose oil, lilac, jasmine, wisteria, apple blossom, or compounds boquets such as spice, aldehydic, woody, oriental, and the like.

Therefore, preferred compositions useful in the present invention may be formulated so as to contain about 95-98% of a water-free mixture comprising:

(a) about 40-55% of a mixture of hydrophillic emollient oils comprising: (i) about 30-50% of the reaction product of a $C_2$-$C_{10}$ polyol having about 2-5˙ free hydroxyl groups with a substituent selected from the group consisting of a fatty acid, a fatty alcohol, a polyoxy(lower)alkanol and mixtures thereof; (ii) about 4-10% of an about 1:1 mixture of a polyoxyalkylene derivative of lanolin and a polyoxyalkylene derivative of a fatty alcohol;

(b) about 40-60% of a mixture of hydrophobic emollient oils comprising: (i) about 15-25% of the benzyl alcohol ester of a fatty acid; (ii) about 10-25% of a fatty alcohol benzoate; and (iii) about 7-20% of a $C_2$-$C_5$ alkanol ester of dimer acid or trimer acid; and (c) minor but effective amounts of an amphoteric detergent.

The present compositions will optionally comprise minor but effective amounts of mineral oil, fragrance and/or a germicide, preferably a germicidal cationic amine salt. The hydrophobic emollient component may optionally comprise about 1-10% mineral oil, e.g. white mineral oil USP.

The emollient formulations are prepared by mixing the oils with the detergents, bactericides and waxes, if any, and heating the stirred emollient mixture to about 45°-85° C. After the mixture has homogenized, it is cooled to about 35°-50° C. and the fragrance added. The germicide may be added at this point, or stirred into the mixture at a lower temperature, if necessary, to preserve its activity. The mixture is then cooled to ambient temperatures, i.e. to about 19°-28° C., and applied by any suitable means to a porous, moisture-absorbent substrate. Any method of textile, paper or foam-coating known in the art may be employed. For example, the composition may be coated onto a sheet of substrate by means of a Meyer rod, a floating knife or doctor blade, or may be rolled onto a foam sheet via a stainless steel roller, or applied by sponging or spraying.

The absorbent sheets useful in the practice of the present invention may be formed from any fibrous or cellular flexible material which exhibits a hydrophile/-lipophile balance (HLB) effective to both effectively absorb moisture from wetted skin surfaces and to retain sufficient amounts of the emollient oil composition to effectively moisturize the skin without leaking or bleeding of the composition during storage. Cellulosic sheets have been found to be particularly well-suited for use as substrates for the present applicators, and are preferably either reinforced or unreinforced one or multiply non-woven paper sheets.

For example, a useful base can be made from a non-woven, cellulosic textile bound with a thermoplastic binder such as air-layered wood fiber Airtex ® toweling (James River Paper Co., Green Bay, Wis.). The nonwoven fiber sheets may be further reinforced with natural or synthetic textile filaments. Textile or foam sheets having an appropriate HLB may also be employed.

Preferably the composition is applied to a cellulosic substrate weighing about 4-5g/ft.² to the extent of about 0.4-15g/ft.², most preferably to the extent of about 0.5-13g/ft.² At higher ratios of composition to substrate, the applicators are suitable for reuse given that the substrate sheet is selected so as to have sufficient wet strength. That is, when used once to dry and moisturize wet hands, an 120 in² applicator having about 12g/ft² of composition thereon may be dried and reused about 1-3 or more times before the emollient composition is depleted.

The invention will be further described by reference to the following detailed examples.

EXAMPLE I. EMOLLIENT COMPOSITIONS

Moisturizing towels were prepared incorporating the formulations summarized on Table I.

TABLE I

Moisturizing Formulations

| Ingredient | Amount (Wt.%) A | B | C |
|---|---|---|---|
| Standamul HE | 29.0 | 29.0 | 29.0 |
| Standamul 302 | 8.6 | 8.6 | 8.6 |
| Standamul 1414E | 3.2 | 3.2 | 3.2 |
| Schercemol TT | 12.9 | 12.7 | 12.9[2] |
| Finsolv TN | 19.5 | 14.0 | 19.5 |
| Dermol 618 | 19.0 | 19.0 | 19.0 |
| Necon CPS-100 | 1.0 | — | — |
| Generol 122E-16 | — | 1.0 | 1.0 |
| Procetyl AWS | 3.0 | 3.0 | 3.0 |
| Lanexol AWS | 3.0 | 3.0 | 3.0 |
| Mineral Oil | — | 5.0 | — |
| Schercamox CAA | 0.5 | 0.7 | — |
| Schercamox DMS | — | 0.8 | — |
| Fragrance[1] | 0.8 | 0.8 | 0.8 |

[1]Firmenich & Co. compound 46-048/B. Equivalent amounts of Firmenich 23929/GE B lavender, Alpine 104.287 Floralistic and R.B. Du Pont K-9060 or H/44 95-4 fragrance could also be substituted.
[2]Equivalent amounts of Schercemol DEIS, DISD, DID or PEG 400 could be substituted.

The ingredients of Col. A of Table I were mixed together in order with agitation and heated to 45°–50° C. The stirred mixture was cooled to 40° C. and the fragrance was added with continued agitation. About 2.25 g of the clear homogeneous mixture was sponged onto a 126 sq. in., 4.3 g sheet of a bonded, single ply, reinforced nonwoven paper towel at about 25° C. to the extent of 4.4g/ft$^2$. The impregnated towel was dry to the touch and exhibited a slightly slippery feeling when rubbed over dry skin. When applied to wetted skin, the towel dried the skin surface while delivering an effective amount of the moisturizing ingredients to the skin surface.

To compound the formulation of column B, Table I, the ingredients minus the fragrance were added in the order listed to the mineral oil and the stirred mixture heated to 60°–65° C. Agitation was continued until the mixture was homogeneous. The stirred mixture was cooled to 37° C. and the fragrance added. Single-ply, filament-reinforced paper towels impregnated with the composition at ambient temperature to the extent of 4.4g/ft$^2$ were smooth and dry to the touch. They readily absorbed moisture when applied to wet skin, having a glossy, nongreasy emollient film on the skin.

The ingredients of column C of Table I were compounded by adding them in the order listed, minus the fragrance, and heating the mixture to 80° C. with agitation. The stirred mixture was cooled to 52° C. and the fragrance was added. When the fragrance had been dispersed, the clear, homogeneous mixture was cooled to 35° C. and applied to paper towelling as described for composition IA. The impregnated towels also effectively dried and moisturized wet skin.

EXAMPLE II

The procedure and ingredients used to prepare the towels of Ex. IB was used with the exception that the amount of Schercemol TT was increased to 12.9% and the Scheramox C-AA was omitted.

EXAMPLE III

Moisturizing towels were prepared using the formulation summarized on Table II.

TABLE II

Moisturizing Formulation

| Ingredient | Wt. (%) | Grams/Batch |
|---|---|---|
| Standamul HE | 29.0 | 116.0 |
| Standamul 302 | 8.6 | 34.4 |
| Standamul 1414-E | 3.2 | 12.8 |
| Crodocal IPM | 12.9 | 51.0 |
| Dermol 105 | 38.5 | 154.0 |
| Generol 122 E-10 | 1.0 | 4.0 |
| Procetyl AWS | 3.0 | 12.0 |
| Lanexol AWS | 3.0 | 12.0 |
| Fragrance | 0.8 | 3.2 |

The ingredients minus the perfume were added in the order listed with agitation and heated to 70° C. until almost clear. The stirred mixture was cooled to 50° C. and the fragrance (R.B. DuPont K-9060) was added. The stirred mixture was cooled to 30° C. and bottled. Portions of the mixture (1.5 and 2.0 g) were sponged onto single ply, nonwoven paper sheets (4.1–4.3 g) at 25° C. The sheets were packaged in metallized paper envelopes. When applied to wet hands, the sheets dried the skin and deposited a thin, clear film of emollients thereon.

While certain representative embodiments of the invention have been described herein for purposes of illustration, it will be apparent to those skilled in the art that modifications therein may be made without departing from the spirit and scope of the invention.

I claim:

1. A cosmetic applicator comprising a porous fibrous or cellular substrate sheet coated with a water-free composition consisting essentially of emollient oils, said oils including:
   (a) about 35–60% of hydrophillic emollient oils including:
      (i) about 25–35% of a polyoxyethylene, ($C_{15}$–$C_{22}$) fatty acid glycerate wherein the polyoxyethylene moiety comprises about 5–10 ethylenoxy moieties;
      (ii) about 5–10% of a $C_6$–$C_{12}$ acid diester of propylene glycol; and
      (iii) about 1–5% of a $C_{12}$–$C_{18}$ fatty acid, $C_{12}$–$C_{18}$ fatty alcohol ester-alkoxylate of a polyethylene glycol comprising about 2–5 ethylenoxy units; and
   (b) about 40–60% of a mixture of hydrophobic emollient oils including:
      (i) about 15–25% of a benzyl alcohol ester of a $C_{10}$–$C_{20}$ fatty acid;
      (ii) about 10–25% of a $C_{12}$–$C_{15}$ alkyl benzoate;
      (iii) about 7–20% of a $C_2$–$C_5$ alkanol ester of dimer acid, trimer acid or mixtures thereof, wherein the interstices between the fibers or the cells of the substrate sheet are substantially free of the composition so that when the applicator is pressed against wet skin under conditions of pressure, the water is absorbed and an emollient film is deposited on said skin, wherein all percentages are by weight of the composition.

2. The applicator of claim 1 wherein the hydrophobic emollient oil further comprises about 1–10% mineral oil.

3. The applicator of claim 1 wherein the composition further comprises about 0.025–2% fragrance.

4. The applicator of claim 1 wherein the composition is coated on to a substrate sheet comprising cellulosic fibers to the extent of about 0.4–15 g/ft$^2$.

5. The applicator of claim 1 wherein the composition further comprises about 0.01–5% of a germicide.

6. The applicator of claim 5 wherein the germicide comprises chlorhexidine gluconate.

7. The applicator of claim 5 which further comprises about 0.1–5% of a $C_{10}$–$C_{20}$-alkyl-di(lower)alkyl amine oxide or a [$C_{10}$–$C_{20}$-alkylamido($C_2$–$C_5$)alkyl]di(lower)alkyl amine oxide.

8. The applicator of claim 1 wherein the ester of dimer or trimer acid comprises triisopropyl trimerate.

9. The applicator of claim 1 wherein the coating composition includes about 95–99% emollient oils.

10. The applicator of claim 1 wherein the hydrophilic emollient oil further comprises about 0.5–5% of a polyoxyethoxylated soya sterol comprising about 5–25 ethanoloxy groups.

11. A method of simultaneously absorbing water from wet skin while applying an effective amount of emollient oils thereto by applying the applicator of claims 1 to said wet skin under conditions of pressure.

* * * * *